US011998239B2

United States Patent
Luo et al.

(10) Patent No.: US 11,998,239 B2
(45) Date of Patent: Jun. 4, 2024

(54) PUNCTURE INSTRUMENT KIT FOR TRANSVAGINAL UTERINE SLING

(71) Applicant: West China Hospital of Sichuan University, Chengdu (CN)

(72) Inventors: Deyi Luo, Chengdu (CN); Hong Shen, Chengdu (CN); Chi Zhang, Chengdu (CN); Xiao Zeng, Chengdu (CN)

(73) Assignee: West China Hospital of Sichuan University, Chengdu (CN)

( * ) Notice: Subject to any disclaimer, the term of this patent is extended or adjusted under 35 U.S.C. 154(b) by 0 days.

(21) Appl. No.: 18/119,847

(22) Filed: Mar. 10, 2023

(65) Prior Publication Data
US 2023/0285051 A1    Sep. 14, 2023

(30) Foreign Application Priority Data

Mar. 11, 2022  (CN) .......................... 202210238188.8

(51) Int. Cl.
*A61B 17/34*       (2006.01)

(52) U.S. Cl.
CPC ...... *A61B 17/3496* (2013.01); *A61B 17/3403* (2013.01); *A61B 17/3417* (2013.01); *A61B 2017/3405* (2013.01); *A61B 2017/3454* (2013.01)

(58) Field of Classification Search
CPC ............. A61F 2/0045; A61B 17/06109; A61B 17/3496; A61B 17/3494; A61B 17/3403; A61B 17/3405; A61B 17/3417; A61B 17/3468; A61B 2017/3454; A61B 5/150534; A61B 5/150633

See application file for complete search history.

(56) References Cited

U.S. PATENT DOCUMENTS

| | | | |
|---|---|---|---|
| 2008/0139877 A1* | 6/2008 | Chu | A61B 17/06066 600/30 |
| 2008/0287971 A1* | 11/2008 | Kuntz | A61F 2/0045 606/151 |
| 2011/0046436 A1* | 2/2011 | Sokol | A61F 2/0045 600/30 |

* cited by examiner

*Primary Examiner* — Ashley L Fishback
(74) *Attorney, Agent, or Firm* — Bayramoglu Law Offices LLC

(57) ABSTRACT

A puncture instrument kit includes a puncture rod, mesh, and sheath. The puncture rod consists of a puncture head, puncture rod body, and handle. One end of the puncture rod body is connected to the handle and the other end is integrated with the puncture head. The puncture head is arc-shaped with an end gradually tapering to form a tip. The tip of the puncture head is circumferentially designed with a groove for fixing a thread during surgery. The puncture head is smoothly connected with the puncture rod body, and the line between the tip of the puncture head and puncture rod body is at an obtuse angle of 130-140° relative to the puncture rod body. The sheath is sleeved on the puncture rod with the rod tip exposed. The mesh and sheath are designed as separate or integrated, and the tip of the puncture rod is provided with a shape-matching detachable silicone protective sleeve.

10 Claims, 2 Drawing Sheets

PUNCTURE INSTRUMENT KIT FOR TRANSVAGINAL UTERINE SLING

CROSS REFERENCE TO THE RELATED APPLICATIONS

This application is based upon and claims priority to Chinese Patent Application No. 202210238188.8, filed on Mar. 11, 2022, the entire contents of which are incorporated herein by reference.

TECHNICAL FIELD

The present disclosure belongs to the field of medical puncture instruments, particularly to a puncture instrument kit for transvaginal uterine sling procedure.

BACKGROUND

Transvaginal uterine sling is developed for treating uterine prolapse and retroverted uterus by lifting the uterus forward and upward to cling to the abdominal wall. At present, the surgical approaches treating uterine prolapse mainly include open surgery, laparoscopic-assisted surgery, and transvaginal surgery. The transvaginal hysteropexy, associated with reduced operation time, less surgical bleeding, faster recovery and better efficacy, can be traced back to 1888. Among the variety of hysteropexy operations, the sacrospinous ligament fixation withstands the test of time. With its popularity, more data have been reported for the exact role of it in terms of anatomical reduction and functional recovery. During the transvaginal surgery, it is very important to use appropriate puncture instruments to help place and fix the "sling material" of uterus. However, there is no dedicated puncture instrument kit for transvaginal uterine sling procedure.

SUMMARY

To overcome the shortcomings of the prior art, the objective of this present disclosure is to provide a puncture instrument kit for transvaginal uterine sling procedure, which can simplify the transvaginal uterine sling procedure and reduce damage to the adjacent tissue during surgery.

The present disclosure provides a puncture instrument kit for transvaginal uterine sling procedure. The puncture instrument kit consists of a puncture rod, mesh, and puncture sheath. The puncture rod includes a puncture head, puncture rod body, and handle. One end of the puncture rod body is connected to the handle and the other end is integrated with the puncture head. The puncture head is arc-shaped with an end gradually tapering to form a tip. The tip of the puncture head is circumferentially provided with a groove for fixing a thread during surgery. The puncture head is smoothly connected with the puncture rod body, and the connecting line between the tip of the puncture head and the connection point of the puncture rod body is at an obtuse angle of 130-140° relative to the puncture rod body. The length ratio of puncture rod body and the puncture head is (1-1.5):1. The puncture sheath is sleeved on the puncture rod with the rod tip exposed. The mesh and puncture sheath are designed as separate or integrated, and the tip of puncture rod is provided with a shape-matching detachable silicone protective sleeve.

Further, the puncture head is arc-shaped with a center angle of 70-80°, preferably 75°.

Further, the puncture head is arc-shaped; the puncture rod body is tangentially connected with the puncture head with the angle of connecting line between the tip of the puncture head and the connection point of the puncture rod body and puncture rod body is 135°.

Further, the puncture sheath is a hollow tube, and the shape of it matches the puncture rod to avoid shifting. An opening (in the form of a vertebral body without a tip) is provided at the part corresponding to the tip of the puncture head to leave the tip of the puncture head exposed. Preferably, a half of the tip of the puncture head, approximately 0.5 cm long, is exposed.

Preferably, the puncture sheath and the puncture rod each are provided with a circular cross-section.

Further, the handle is provided with a non-slip concave-convex structure.

Preferably, the mesh and the puncture sheath are independent of each other or connected together. When the mesh and the puncture sheath are independent of each other, the mesh and the puncture sheath are used in combination. When the mesh and the puncture sheath are connected together, the mesh is fixed at the tail of the puncture sheath.

Further, the length ratio of the puncture rod to the puncture head is (1-1.5):1; the puncture sheath covers the puncture head partially and one-third of the puncture rod body.

Further, the length of the puncture head is 9 cm, and the length of the tip is 1 cm; the total length of the puncture rod body and the puncture head ranges from 20 to 25 cm and the diameter of the rod is 10 Fr; the diameter of the puncture head is gradually reduced to form the tip of the puncture head from the joint of the puncture head and the puncture rod body. The diameter of the puncture sheath is 12 Fr and the length ranges from 10 to 14 cm. The material of puncture rod is preferred to medical grade alloy, and the material of puncture sheath is preferred to medical grade polyvinyl chloride (PVC). The mesh is configured to fix the uterus, preferably 20 cm×2 cm medical grade polypropylene (PP). The puncture sheath is configured to ease the placement of the mesh. The mesh and puncture sheath are disposable.

To avoid contamination, the puncture instrument kit further includes an integral storage box with a concave cavity matching the shape of the puncture rod, the puncture sheath and the mesh, and a packaging box for sealing the storage box.

The method of using the puncture instrument kit during surgery is as follows. At the beginning of the operation, the puncture sheath is sheathed on the puncture rod, and then the puncture rod is inserted into the uterine cavity through the cervix. After adjusting the position of the puncture rod, it is driven towards the abdominal wall. The skin is cut using a scalpel when the puncture head reaches a subcutaneous region. Keep driving the puncture rod until the puncture head penetrate the abdominal wall. According to the different settings of the puncture instrument kit, the subsequent steps are as follows.

1. When the puncture sheath and the mesh are integral, the puncture rod is withdrawn directly. The puncture sheath is pulled ventrally until the end of the mesh is in the appropriate position and the mesh is secured. Then the excess parts of the mesh and the puncture sheath are cut off.

2. When the puncture sheath and the mesh are independent of each other, the operative procedure is processed as followed: firstly, a lasso of a thread is fixed in the groove at the tip of the puncture head, and then the puncture rod is withdrawn until the thread reaches the cervix. The fixed thread is released from the puncture head and is attached to one end of the mesh. Pulling the free end of the thread until the mesh reaches the outside of the abdominal wall, and then the sheath is removed. After adjusting the mesh to an appropriate place, the mesh is fixed and the excess part of mesh is cut off.

Based on the same technical concept, the present disclosure further provides a puncture instrument kit for transvaginal uterine sling. It differs from that above in that, the tip of the puncture head is not provided with the groove for fixing the thread during surgery, and the mesh is separated from the puncture sheath. In addition, the puncture instrument kit in this embodiment further includes a guide device. The guide device includes a guide rod and a guide frame located at an end of the guide rod and integrated with the guide rod.

Further, the guide rod is longer than the puncture sheath.

Further, the guide frame is a diamond-shaped frame for pulling a thread. The guide device is preferably made of medical grade plastic.

The present disclosure has the following beneficial effects over the prior art:

1. In the present disclosure, the angle between the puncture head and the puncture rod body fully meets the puncture requirements of transvaginal uterine sling procedure, which enables easy access to the uterine cavity and the adjustment of uterine position.

2. In the present disclosure, the diameter and length of the puncture rod body are reasonably designed. If the puncture rod is too thick, it will increase tissue damage during the puncture. If the puncture rod is too thin, it will limit the progress of the operation. If the puncture rod is too long, it will be inconvenient in surgery. If the puncture rod is too short, it will limit the puncture process.

3. In the present disclosure, the tip of the puncture head is exposed, and the exposed length is designed reasonably, which can meet the requirement of puncture process when the tissue structure is thicker and denser. Meanwhile, the shape and the diameter of the puncture sheath are reasonably designed to avoid the displacement of the puncture sheath and the tissue embedding between the puncture rod and the puncture sheath.

4. The present disclosure integrates the mesh with the puncture sheath, which facilitates the placement of the mesh. After successful puncture, the mesh can be placed in the puncture channel by directly pulling the puncture sheath.

Figure 1:
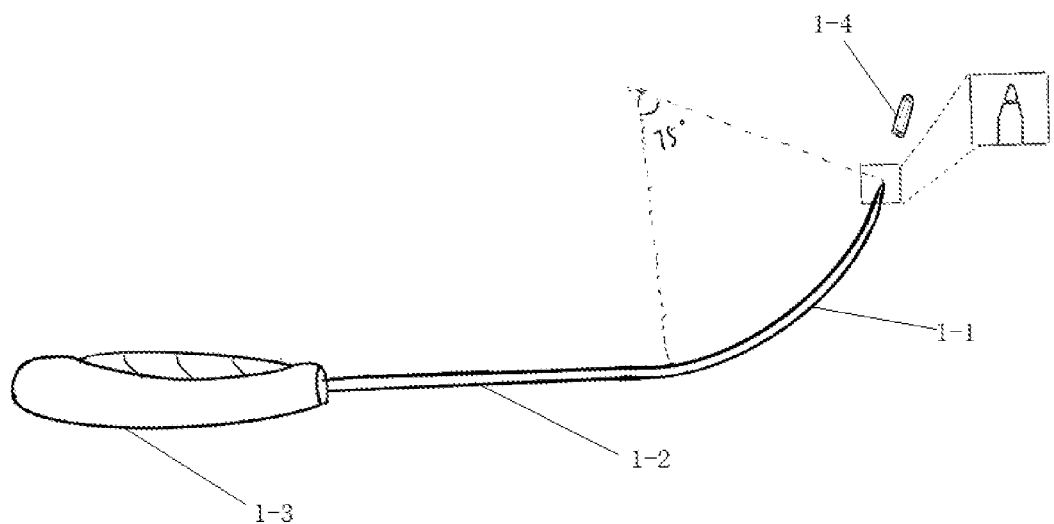
FIG. 1 is a structural diagram of a puncture rod according to the present disclosure.
Figure 2:
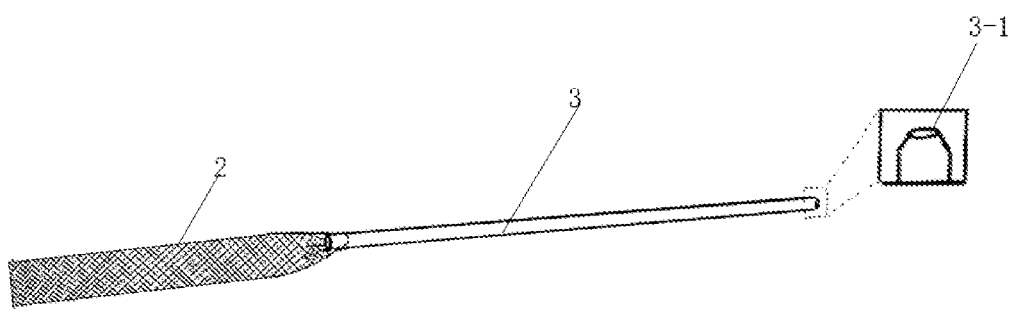
FIG. 2 is a structural diagram of a puncture sheath and a mesh that are integrated with each other according to the present disclosure.
Figure 3:
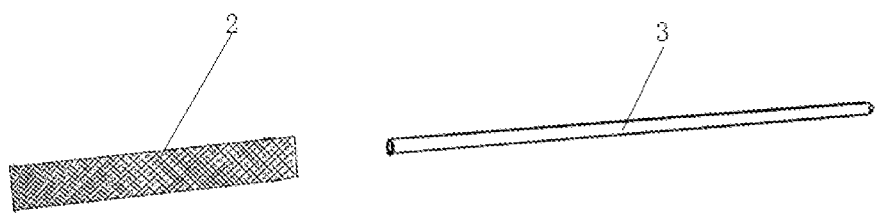
FIG. 3 is a structural diagram of a puncture sheath and a mesh that are separated from each other according to the present disclosure.
Figure 4:
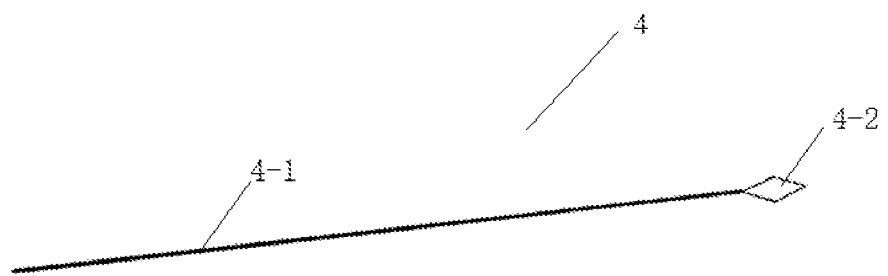
FIG. 4 is a structural diagram of a guide device according to the present disclosure.

REFERENCE NUMERALS 1-1. puncture head; 1-2. puncture rod body; 1-3. handle; 1-4. detachable silicone protective sleeve; 2. mesh; 3. puncture sheath; 3-1. opening; 4. guide device; 4-1. guide rod and 4-2. guide frame.

DETAILED DESCRIPTION OF THE EMBODIMENTS

The present disclosure is further described below by referring to the embodiments. It is to be noted that the embodiments are merely intended to further explain the present disclosure, rather than to limit the protection scope of the present disclosure. Any unessential improvement and adjustment made to the present disclosure according to the contents of the present disclosure should be included in the protection scope of the present disclosure.

Embodiment 1

In this embodiment, a puncture instrument kit for transvaginal uterine sling includes a puncture rod, mesh 2, and puncture sheath 3, where the puncture rod includes puncture head 1-1, puncture rod body 1-2, and handle 1-3; the puncture head, the puncture rod body, and the handle are connected. One end of the puncture rod body is connected with the handle and the other end is integrated with the puncture head. The puncture head is arc-shaped, and the end of the arc-shaped puncture head gradually tapers to a tip. The tip of the puncture head is circumferentially provided with a groove for fixing a thread during surgery. The puncture rod body is tangentially connected to the puncture head. The connecting line between the tip of the puncture head and the connection point of the puncture rod body forms an obtuse angle of 135° with the puncture rod body, and the arc-shaped puncture head corresponds to a center angle of 75°. The puncture sheath is partially sheathed on the puncture rod body with the tip of the puncture head and the groove on the tip is exposed outside the puncture sheath. The mesh is bonded to the tail of the puncture sheath. The puncture sheath matches the shape (e.g., corresponds to the shape) of the puncture rod body and the puncture head. The head of the puncture sheath corresponding to the puncture head forms opening 3-1. The opening is of a conical frustum shape without tip, enabling the tip of the puncture head to be exposed for about 0.5 cm 3-1. The handle is provided with a non-slip concave-convex structure. The tip of the puncture head is provided with a detachable silicone protective sleeve 1-4, the shape of the detachable silicone protective sleeve correspond to the shape of the tip.

The length of the puncture head is 9 cm, and the length of the tip is 1 cm. The total length of the puncture rod body and the puncture head is 25 cm and the diameter of the puncture rod is 10 Fr. The diameter of the puncture head is gradually reduced from the joint between the puncture head and the puncture rod body to the tip of the puncture head. The diameter and length of the puncture sheath is 12 Fr and 12 cm, separately. The puncture rod is preferably made of a medical alloy, and the puncture sheath is preferably made of medical grade polyvinyl chloride (PVC). The mesh for fixing the uterus is preferably made of a 20 cm×2 cm medical grade polypropylene (PP). The mesh and puncture sheath are both disposable.

A method of using the puncture instrument kit of the present disclosure during surgery is as follows. At the beginning of the operation, the puncture sheath is sheathed on the puncture rod, and then the puncture rod is inserted into a uterine cavity through a cervix. The position of the puncture rod is adjusted, and the puncture rod is driven to puncture through tissue toward the abdominal wall. When the puncture head reaches the subcutaneous region, the skin is cut by a scalpel to enable the puncture head penetrate the abdominal wall. The puncture rod is then withdrawn directly. The puncture sheath is pulled through the abdominal wall until the mesh is at an appropriate position. The mesh is fixed, and excess parts of the mesh and the puncture sheath are cut off.

By using the puncture instrument kit of the present disclosure to perform transvaginal uterine sling, the pelvic floor reconstruction time for treating uterine prolapse can be shortened to about 20 min, the amount of bleeding can be reduced to about 20 ml, and the postoperative hospital stay is about 2 days.

Embodiment 2

In this embodiment, the puncture instrument kit for transvaginal uterine sling differs from that in Embodiment 1 in that, the mesh and the puncture sheath are separated and are used in combination.

A method of using the puncture instrument kit of the present disclosure in surgery is as follows. At the beginning of the operation, the puncture sheath is sheathed on the puncture rod, and the puncture rod is inserted into a uterine cavity through a cervix. The position of the puncture rod is adjusted, and the puncture rod is driven to puncture toward the abdominal wall. When the puncture head reaches the subcutaneous region, the skin is cut by a scalpel to enable the puncture head penetrate the abdominal wall. A lasso of a thread is secured (e.g., fixed) in the groove at the tip of the puncture head. The puncture rod is withdrawn until the thread reaches the cervix. The fixed thread is removed from the puncture head and is fixed to one end of the mesh. Pulling the free end of the thread until the mesh reaches the outside of the abdominal wall. Then the puncture sheath is withdrawn. The mesh is fixed and adjusted to an appropriate position. An excess part of the mesh is cut off.

Embodiment 3

In this embodiment, the puncture instrument kit for transvaginal uterine sling differs from that in Embodiment 1 in that, the tip of the puncture head is not provided with the groove for fixing the thread during surgery, and the mesh is separated from the puncture sheath. In addition, the puncture instrument kit in this embodiment further includes guide device 4. The guide device includes guide rod 4-1 and guide frame 4-2 which located at an end of the guide rod and integrated with it. The guide rod is longer than the puncture sheath. The guide frame is diamond-shaped. The guide device is preferably made of medical grade plastic.

A method of using the puncture instrument kit during surgery of the present disclosure is as follows. At the beginning of the operation, the puncture sheath is sheathed on the puncture rod, and the puncture rod is inserted into a uterine cavity through a cervix. The position of the puncture rod is adjusted, and the puncture rod is driven to puncture towards the abdominal wall. When the puncture head reaches the subcutaneous region, the skin is cut using a scalpel to enable the puncture head penetrate the abdominal wall. After the puncture rod is withdrawn, the diamond-shaped end of the guide device is inserted into the puncture sheath from the upper end (abdominal side) to a lower end (cervical side) until the diamond-shaped end reaches the lower end of the puncture sheath. One end of the thread is fixed to one end of the mesh, and the other end of the thread is inserted into the diamond frame of the guide device. Then the guide device is withdrawn. With the withdrawal of the guide device, the thread is placed into the puncture sheath cavity. Pulling the free end of the thread until the mesh reaches the outside of the abdominal wall. The puncture sheath is withdrawn, and then the mesh is fixed. After the mesh is adjusted to an appropriate position, the excess part of the mesh is cut off.

What is claimed is:

1. A puncture instrument kit for transvaginal uterine sling, comprising a puncture rod, mesh, and puncture sheath, wherein the puncture rod comprises a puncture head, a puncture rod body, and a handle; the puncture head, the puncture rod body, and the handle are connected; the puncture rod body comprises one end connected with the handle and the other end integrated with the puncture head; the puncture head is curved and has an end gradually tapering to form a tip; the tip of the puncture head is circumferentially provided with a groove for fixing a thread during surgery; the puncture head is smoothly connected with a connection point of the puncture rod body, and a connecting line between the tip of the puncture head and the connection point of the puncture rod body forms an obtuse angle of 130-140° relative to the puncture rod body, wherein the connection point of the puncture rod body is a position where the puncture head and the puncture rod body are connected; the length ratio of the puncture rod body and the puncture head is (1-1.5):1; the puncture sheath is sleeved on the puncture rod and covers the puncture head partially and the puncture rod body partially; the tip of the puncture head and the groove on the tip extend from the puncture sheath; the mesh and the puncture sheath are separated from each other or connected together; and the tip of the puncture head is provided with a detachable silicone protective sleeve, the shape of the detachable silicone protective sleeve correspond to the shape of the tip.

2. The puncture instrument kit for the transvaginal uterine sling according to claim 1, wherein the puncture sheath covers one-third of the puncture rod body.

3. The puncture instrument kit for the transvaginal uterine sling according to claim 1, wherein the puncture head is arc-shaped and corresponds to a center angle of 70-80°.

4. The puncture instrument kit for the transvaginal uterine sling according to claim 1, wherein the puncture sheath is a tube, a shape and size of the tube correspond to a shape and size of the puncture rod, and a part of the puncture sheath corresponding to the tip of the puncture head forms an opening; and a part of the tip of the puncture head extends from the opening.

5. The puncture instrument kit for the transvaginal uterine sling according to claim 4, wherein the tip of the puncture head has a length of 0.5 cm extending from the opening.

6. The puncture instrument kit for the transvaginal uterine sling according to claim 1, wherein the puncture head is arc-shaped; the puncture rod body is tangentially connected with the puncture head; and the connecting line between the tip of the puncture head and the connection point of the puncture rod body forms an obtuse angle of 135° relative to the puncture rod body, wherein the connection point of the puncture rod body is the position where the puncture head and the puncture rod body are connected.

7. The puncture instrument kit for the transvaginal uterine sling according to claim 1, wherein cross-sections of the puncture sheath and the puncture rod are circular.

8. The puncture instrument kit for the transvaginal uterine sling according to claim 1, wherein the handle is provided with a non-slip concave-convex structure.

9. The puncture instrument kit for the transvaginal uterine sling according to claim 1, wherein the mesh and the puncture sheath are separated from each other or connected together; when the mesh and the puncture sheath are separated from each other, the mesh and the puncture sheath are used in combination; and when the mesh and the puncture sheath are connected together, the mesh is bonded to a tail of the puncture sheath.

10. The puncture instrument kit for the transvaginal uterine sling according to claim 1, wherein the puncture head has a length of 9 cm, and the tip has a length of 1 cm; the puncture rod body and the puncture head have a total length of 20-25 cm and a diameter of 10 Fr; the diameter of the puncture head is gradually reduced from a joint between the puncture head and the puncture rod body to the tip of the puncture head; the puncture sheath has a diameter of 12 Fr and a length of 10-12 cm; and the mesh is made of 20 cm×2 cm medical grade polypropylene (PP).

* * * * *